US005525295A

United States Patent [19]
Pflug et al.

[11] Patent Number: 5,525,295
[45] Date of Patent: Jun. 11, 1996

[54] BARRIER ISOLATION SYSTEM

[75] Inventors: Irving J. Pflug, Minneapolis; Allan B. Larson, Mound; Hans L. Melgaard, North Oaks, all of Minn.

[73] Assignees: Despatch Industries Limited Partnership, Minneapolis; TL Systems Corporation, Brooklyn Park, both of Minn.

[21] Appl. No.: 937,211

[22] Filed: Aug. 27, 1992

Related U.S. Application Data

[63] Continuation-in-part of Ser. No. 880,206, May 6, 1992, abandoned.

[51] Int. Cl.$^6$ ............................................. A61L 2/08
[52] U.S. Cl. ............................. 422/27; 422/26; 422/31; 422/302; 422/307
[58] Field of Search ................... 422/26, 295, 298, 422/299, 300, 302, 304, 307, 308, 27, 31; 432/152, 72

[56] References Cited

U.S. PATENT DOCUMENTS

| | | | |
|---|---|---|---|
| 3,450,487 | 6/1969 | Wallden | 422/298 |
| 4,225,556 | 9/1980 | Löthman et al. | 422/28 |
| 4,424,189 | 1/1984 | Hick | 422/27 |
| 4,707,334 | 11/1987 | Gerhard | 422/31 X |
| 4,821,866 | 4/1989 | Melgaard | 15/301 |
| 4,846,669 | 6/1989 | Melgaard | 432/59 |
| 4,894,207 | 1/1990 | Archer et al. | 422/295 |
| 4,988,288 | 1/1991 | Melgaard | 432/72 |
| 4,992,247 | 2/1991 | Foti | 422/304 |
| 5,007,232 | 4/1991 | Caudill | 53/426 |
| 5,064,614 | 11/1991 | Reiss et al. | 422/304 |
| 5,095,925 | 3/1992 | Elledge et al. | 422/292 |
| 5,152,968 | 10/1992 | Foti et al. | 422/31 X |

OTHER PUBLICATIONS

Speech presented at ISPE Expo 89 May 8, 1989 entitled, "The Historic and Current Status of Dry Heat Sterilization and Depyrogenation", author: Hans L. Melgaard.

Primary Examiner—Robert J. Warden
Assistant Examiner—Robert Carpenter
Attorney, Agent, or Firm—Fredrikson & Byron

[57] ABSTRACT

A microbial barrier isolation system for enclosing and decontaminating equipment so that the equipment may be used in handling or otherwise contacting biologically-sensitive materials such as parenteral solutions and solids. The barrier system is formed with a lower cavity, an upper chamber separated from the inner cavity by filters, an air return conduit, means for supplying dry, heated air to heat the system and means for using steam and hydrogen peroxide to decontaminate the internal parts of the system. The decontamination process involves using dry air to heat the internal equipment of the system to reduce water condensation and then introducing saturated steam and peroxide at a positive pressure slightly above atmospheric pressure. The internal equipment, including all surfaces, is exposed to the steam and peroxide sterilant for a sufficient time to decontaminate the equipment and the system is cooled down with cool, sterile air.

16 Claims, 3 Drawing Sheets

BARRIER ISOLATION SYSTEM

The present application is a continuation-in-part application of applicants' U.S. patent application Ser. No. 07/880,206 filed May 6, 1992, now abandoned.

FIELD OF THE INVENTION

The present invention generally relates to material treatment ovens and, more particularly, relates to a means for decontaminating equipment used in the pharmaceutical industry.

BACKGROUND OF THE INVENTION

An increasing number of materials sold on the market today are sensitive to contamination by viable microorganisms. Drugs that are injected into living tissue or blood (parenteral solutions) are particularly sensitive to contamination by such microorganisms. The current standard set by the U.S. Food and Drug Administration (FDA) regarding the probability of having a viable microorganism present in an aseptically-assembled product is generally on the order of one in one thousand ($10^{x3}$). The FDA would like to increase this standard to one in one million ($10^{x6}$). Consequently, the FDA is encouraging change in parenteral drug manufacturing that will decrease the probability of contamination.

There are several paths available to decreasing the probability of viable microorganisms in a parenteral drug product. One of these paths which is encouraged by the FDA is the use of terminal sterilization where possible for parenteral-type pharmaceutical products. Many such products, however, are temperature sensitive, i.e., a temperature that is significantly greater than ambient temperatures will rapidly degrade their efficacy or activity. For products that cannot be terminally sterilized, improved aseptic manufacturing systems are the only alternative.

One method of controlling the contamination of parenteral drug products involves sterilizing the products prior to filling. The products are then aseptically filled and the containers closed within a decontaminated box that is absent of any workers. Such a system has the potential of meeting the reduced microbial contamination levels sought by the FDA. This type of system is called a barrier system since there is a barrier between the product and the equipment operator.

For a barrier system to help meet the new FDA objectives, it must have isolation integrity and be able to maintain this isolation integrity during operation. The decontamination of barrier systems is a critical part of the process. A variety of techniques are known in the art for effectively decontaminating filling lines and the like which are used in connection with pharmaceutical products. Chemicals may be used for this decontamination, but they are hazardous and can leave residue. Any active molecule that has the potential to come into contact with a sensitive product can potentially degrade or contaminate that product. Accordingly, an effective means of decontaminating the equipment inside the barrier that only utilizes temperature and environmental conditions that will not adversely affect the equipment or its component parts should speed this needed development.

To avoid degrading the efficacy of a pharmaceutical product by overheating, however, elevated-temperature decontamination generally must be carried out when the equipment is not being used to handle the product. Unfortunately, this essentially represents "down time" for these pieces of equipment, preventing them from performing their intended function during the decontamination process. Accordingly, it would be desirable to provide a system for decontamination equipment used for handling biologically sensitive products which achieves a high level of decontamination with a minimum of down time for the equipment.

SUMMARY OF THE INVENTION

The present invention relates to a microbial barrier isolation system for enclosing and decontaminating equipment used for packaging pharmaceutical products. The barrier system is formed with an inner cavity, an upper chamber separated from the inner cavity by filters, an air return conduit, means for supplying dry, heated air to heat the system and means for using steam or a mixture of steam and hydrogen peroxide to decontaminate the internal parts of the system.

The present invention also includes a method for decontaminating equipment so that the equipment may be used in handling or otherwise contacting biologically-sensitive materials such as parenteral solutions and solids. The decontamination process involves using dry air to heat the internal equipment of the system to reduce water condensation and then introducing saturated steam at a positive pressure slightly above atmospheric pressure, about ¼" W.C. If so desired, hydrogen peroxide may be introduced into the steam supply to provide a combination of steam and hydrogen peroxide to the inner cavity. The internal equipment, including all surfaces, is exposed to the steam, or steam/hydrogen peroxide mixture, for a sufficient time to decontaminate the equipment and the system is then cooled down with cool, sterile air.

In accordance with this method, hot air is introduced into the upper chamber and passed through filters and into the inner cavity before being returned to the hot air source through the air-return conduit. Once the filters are sufficiently heated so that no condensation will form on them, steam is introduced into the upper chamber through a perforated conduit. If hydrogen peroxide is to be used, the hydrogen peroxide may be introduced into the saturated steam supply at this time. The saturated steam passes through the filters and fills the enclosed inner cavity to decontaminate all of the equipment and surfaces within the cavity. After this saturated steam environment is maintained for a sufficient period of time to achieve the desired degree of decontamination, the steam is circulated out of the barrier system and cold, dry HEPA-filtered air is introduced to cool down the cavity and its contents and to evaporate any residual condensation.

DETAILED DESCRIPTION OF THE PREFERRED EMBODIMENTS

The barrier isolation system of the present invention is suitable for use as part of a material handling system for packaging pharmaceuticals or other biologically sensitive materials in suitable containers or vials. To eliminate the risk of introducing microorganisms into the products placed therein, the vials are typically sterilized in a hot air tunnel before being filled. To avoid microbial contamination during the handling of these materials, the equipment coming into contact with the product or the vials must also be decontaminated. The present invention discloses a method of achieving such equipment decontamination.

Figure 1:
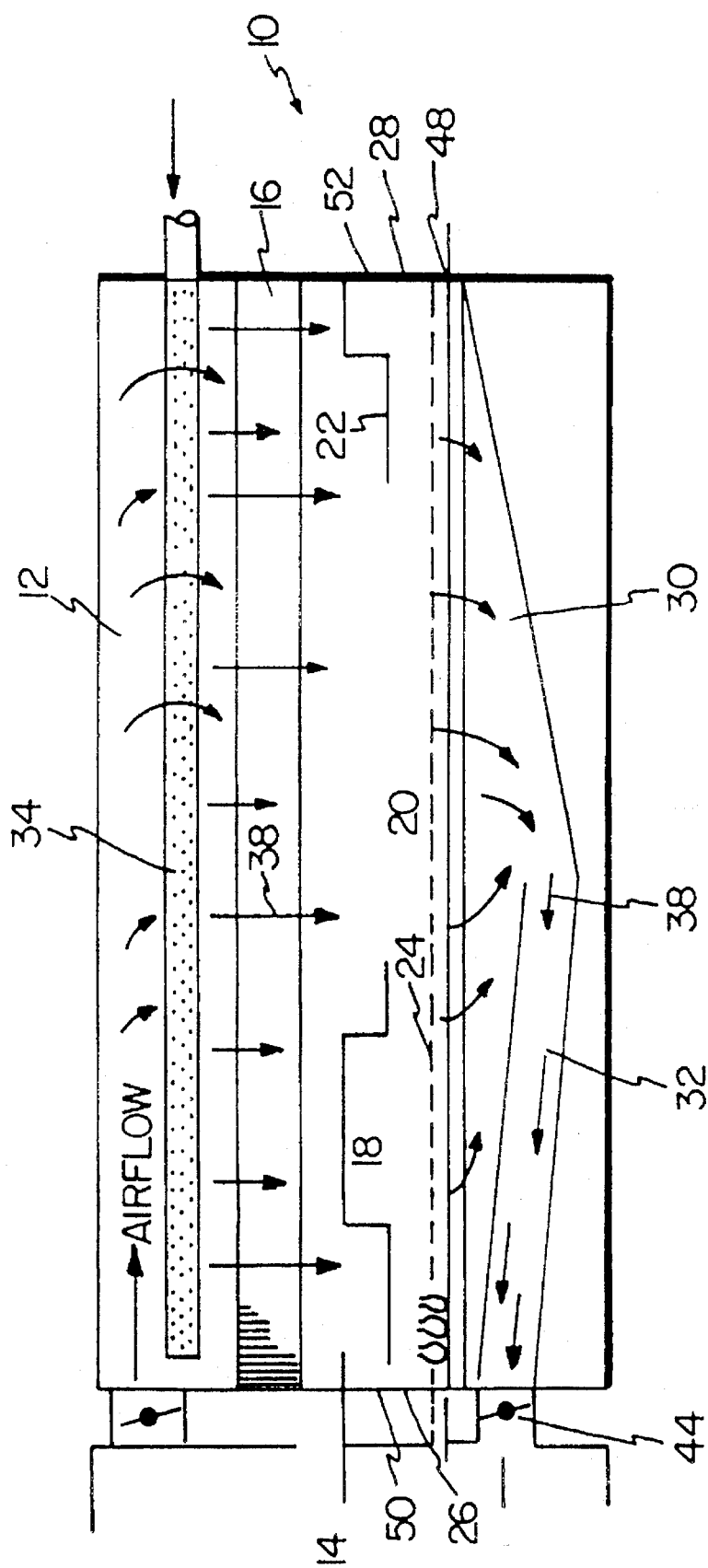
FIG. 1 is schematic elevational view of a barrier isolation system of the invention with the side portion removed to show interior detail.

The barrier isolation system, designated 10 in FIG. 1, includes a housing defining a generally closed system within which the material handling equipment may be contained. As explained below, this closed system essentially serves as a barrier to isolate the equipment from the external environment, thereby preventing contamination from airborne microorganisms and maintaining the equipment in a germ-free state.

The housing preferably contains outer walls 11 which are desirably insulated with an appropriate material. Side walls 15 desirably reside in the interior of the housing adjacent the outer walls 11 so that a space is defined between them. The system 10 may include an upper chamber 12 and a lower, inner cavity 14, with the upper chamber 12 desirably being disposed generally vertically above the inner cavity 14. The inner cavity 14 desirably extends along the entire length of the system over a generally horizontal path. Although the upper chamber 12 may be of any desired shape, in the preferred embodiment shown in FIG. 1 it comprises a generally horizontally-oriented space which extends along the length of the inner cavity 14 and is disposed above the inner cavity 14.

A plurality of filters 16 extend generally horizontal along a length of the interior of the housing and divide the upper chamber 12 and the inner cavity 14 so that any air or steam entering the upper chamber 12 must pass through these filters 16 prior to passing into the inner cavity 14. These filters 16 may be of any construction which reduces or eliminates the passage of microorganisms from the air supply in the upper chamber 12 to the inner cavity 14. Desirably, the filters 16 are HEPA filters, which are readily commercially available, due to their proven reliability and efficacy in high-temperature applications. In the embodiment shown in FIG. 1, wherein the upper chamber 12 and the inner cavity 14 are both generally horizontally oriented, the filters 16 desirably extend generally horizontally between the upper chamber 12 and the inner cavity 14. The filters should desirably engage the walls of the housing to effectively seal the upper chamber 12 from the inner cavity 14, thereby preventing air or steam from simply passing around the filters and into the inner cavity 14. In the preferred embodiment shown in the drawings, such a seal between the inner cavity 14 and the upper chamber 12 is achieved by abutting the filters against air return ducts 62, located above a portion of the side walls 15, and against the end walls 50, 52 of the housing.

Any desired material handling equipment may be positioned within the inner cavity 14. The cavity 14 desirably includes a floor 48 for supporting this equipment. The type of equipment present within the cavity 14 will vary depending upon the characteristics and requirements of the product as well as the intended function of the equipment. For example, if the equipment is intended for use in filling containers with liquid pharmaceuticals or the like, it may include a filler 18 for filling the containers with pharmaceutical products, a device 20 for measuring the weight of the filled containers and a capper 22 for applying a suitable seal on the containers. Such filling equipment is known in the art and need not be discussed in detail here.

As noted above, the inner cavity 14 desirably spans the entire length of the barrier system 10. Conveyor means 24 for conveying containers or the like desirably extends along the entire length of the inner cavity 14. The precise nature of the conveyor means will depend on the nature of the articles being conveyed; a standard conveyor belt sized to carry the desired containers has been found to work quite well.

At each end of the inner cavity 14, access doors 26, 28 are provided through the end walls 50, 52, allowing materials to enter the cavity 14 at one end for handling or processing and exit the cavity 14 at the other end after being processed. The access doors 26, 28 are desirably double walled and, in a preferred embodiment, contain transparent windows for viewing the interior of the system. These windows may, for instance, be formed of Lexan, a trade name for a type of plexiglass. The conveyor means 24 desirably receives the materials at the inlet door 26 and transports them through the cavity 14 along a predetermined path for access by the equipment. The conveyor means 24 may urge the final product out of the cavity 14 through the outlet door 28. Although a generally linear configuration is shown in FIG. 1 with the inlet and outlet doors being positioned at opposite ends of the housing along a straight, horizontal line, it is to be understood that this construction may be varied. For example, the path of the conveyor means may be generally L-shaped and the outlet door 28 may be disposed laterally of the inlet door 26.

An air return conduit 30 is in fluid communication with the inner cavity 14 such that fluid within the inner cavity 14 can be passed on to the return conduit 30. In one embodiment, the floor 48 of the inner cavity 14 is perforated to define a plurality of passageways between the inner cavity 14 and return conduit 30. Since the upper chamber 12 is disposed directly above the inner cavity 14, gases passing through the cavity 14 may establish a generally laminar flow pattern between the upper chamber 12 and the return conduit 30. This relatively uniformly distributes the flow of gases from the upper chamber 12 to the return conduit 30 along the length and width of the cavity 14, enabling a more uniform heating of the equipment.

The return conduit 30 is desirably structured to receive air or other fluids from the inner cavity 14 and direct these fluids out of the barrier system 10. In the preferred embodiment of FIG. 1, the mouth of the return conduit 30 is expansive enough to cover a substantial amount of the area underneath the floor 48 of the inner cavity 14. The return conduit 30 is desirably shaped so that the air it receives is funneled into a return channel 32, and a control valve 44, such as a mechanized damper, may be provided in this channel for controlling the flow rate of gases exiting the housing. If so desired, the return channel 32 may be connected to an external recirculation system for recirculating the gasses passing through the cavity 14 back to the upper chamber 12.

The barrier system 10 allows steam or other decontaminating gases to be introduced into the interior of the housing. In a preferred embodiment, a steam conduit 34 adapted to transport saturated steam extends from a steam source (not shown), which may be positioned externally of the housing, into the upper chamber 12. Control means, for instance, a check valve, regulates the entrance of the steam into the housing. Any appropriate method for allowing the steam to exit the conduit 34 into the upper chamber 12 will suffice. In the preferred embodiment, the portion of the conduit 34 located inside the upper chamber 12 is perforated with multiple apertures 36 spaced uniformly along its length to permit steam within the conduit 34 to be relatively uniformly distributed within the upper chamber 12. This perforated conduit desirably extends along almost the entire length of the upper chamber 12. As with the perforations in the floor, this encourages laminar flow through the cavity 14.

Whereas the barrier system of FIG. 1 may be designed to be used with a single decontamination gas, most preferably saturated steam, an alternative embodiment of the invention is adapted to deliver either saturated steam alone or a combination of saturated steam and hydrogen peroxide to the upper chamber 12. Although the peroxide may be introduced to the steam flow at any point and in any desired manner, such as at the steam source (not shown), it is preferred that the peroxide be introduced to the steam flow at a location adjacent to steam tube 34. In this embodiment, the peroxide is introduced to the steam supply by means of an atomizer. The atomizer may include a pressurized steam line and an inlet for peroxide which is in fluid in connection with a peroxide supply (not shown). The peroxide mixes with the steam within the atomizer and the atomizer includes a nozzle at its forward end. By passing the hydrogen peroxide/steam mixture through the nozzle under pressure, the peroxide will be effectively atomized.

This atomized mixture of steam and hydrogen peroxide may then be mixed with the balance of the steam supply prior to introduction to the steam conduit 34. In order to insure efficient distribution of the peroxide within the steam supply, the nozzle of the atomizer may be positioned within a small mixing chamber. This mixing chamber should be adapted to insure that the hydrogen peroxide which has been atomized by the nozzle is thoroughly mixed with the steam prior to passing this combined hydrogen peroxide/steam decontamination fluid into the steam conduit 34. The steam conduit 34 may be structured substantially the same as described above in connection with FIG. 1, insuring that the mixture of hydrogen peroxide and steam is evenly distributed throughout the inner cavity 14 to decontaminate any equipment contained therein.

One advantage of this embodiment of the invention is that it may be operated either with or without hydrogen peroxide. If it is preferred that a particular decontamination operation be carried out only with steam, the supply of steam and hydrogen peroxide to the atomizer may be shut off by a suitable control means and only steam will pass through the mixing chamber into the steam tube 34 for delivery to the barrier system 10. The use of steam alone may be necessary where the product being packaged within the inner cavity 14 is particularly sensitive to chemical agents such as hydrogen peroxide. If the product is not overly sensitive to hydrogen peroxide, steam and hydrogen peroxide may be supplied to the atomizer to speed up the decontamination of the equipment, as explained more fully below.

If the hydrogen peroxide introduced to the steam supply through the atomizer is significantly cooler than the steam, this will obviously tend to reduce the temperature of the steam. Since this could lead to condensation of the steam within the barrier system 10, it is preferred that the hydrogen peroxide by preheated prior to introduction to the atomizer. Accordingly, it may be desirable to provide a separate heat supply (not shown), such as a dedicated heating coil associated with the hydrogen peroxide supply, to preheat the hydrogen peroxide before it is introduced to the atomizer.

Alternatively, the additional heat necessitated by the introduction of hydrogen peroxide to the steam supply may be provided by heaters located downstream of the chamber. The heaters, for example, may be disposed in the upper chamber 12. These heaters should be spaced along the length of the chamber 12 and are desirably positioned adjacent the steam delivery conduit 34. This will insure that the hydrogen peroxide/steam mixture is maintained at an adequate elevated temperature to prevent condensation of the steam within the system, and particularly within the filters 16.

An air recirculation loop, shown in phantom lines at 38, drives air through the filters 16 and over the equipment in the inner cavity 14. The air recirculation loop desirably includes at least a heating element for heating air introduced to the barrier system, a blower for driving air through the loop, and a filter for filtering air introduced into the system 10. If so desired, the loop may also be provided with a cooling coil or the like to permit the barrier system to be cooled more rapidly, reducing the down time of the equipment contained therein. A suitable design of such a loop 38 is shown in Melgaard's U.S. Pat. No. 4,988,288, the teachings of which are incorporated herein by reference.

In one preferred embodiment, the upper chamber 12 includes air supply ducts 60 and air return ducts 62 for assisting in controlling and directing the recirculation loop. In an alternate embodiment, the space between the outer walls 11 and the side walls 15 defines a conduit 63 which may direct air flow upwardly from the inner cavity 14 to the air return ducts 62. The air flowing through the conduit 63 is desirably controlled with baffles located in the side walls 15.

In order to decrease the chances of contamination, most of the equipment employed in the recirculation loop (blowers, heating element, cooling coil, etc.) is desirably located outside the housing of the barrier system 10. Additionally, as the barrier system 10 of the present invention is adaptable for use as part of an overall material handling and treatment process, frequently the recirculation equipment will already be present in another portion of the process.. Such an embodiment is depicted in U.S. Pat. No. 4,988,288, noted above, in which the hot and cool air cycles are produced in separate recirculation chambers. Thus, in one preferred embodiment, an air recirculation loop is created outside the barrier system 10 and mechanized dampers or other control devices are used to control the entrance of the air into the upper chamber 12 and the removal of the air through the channel 32 or air return ducts 62.

Figure 2:
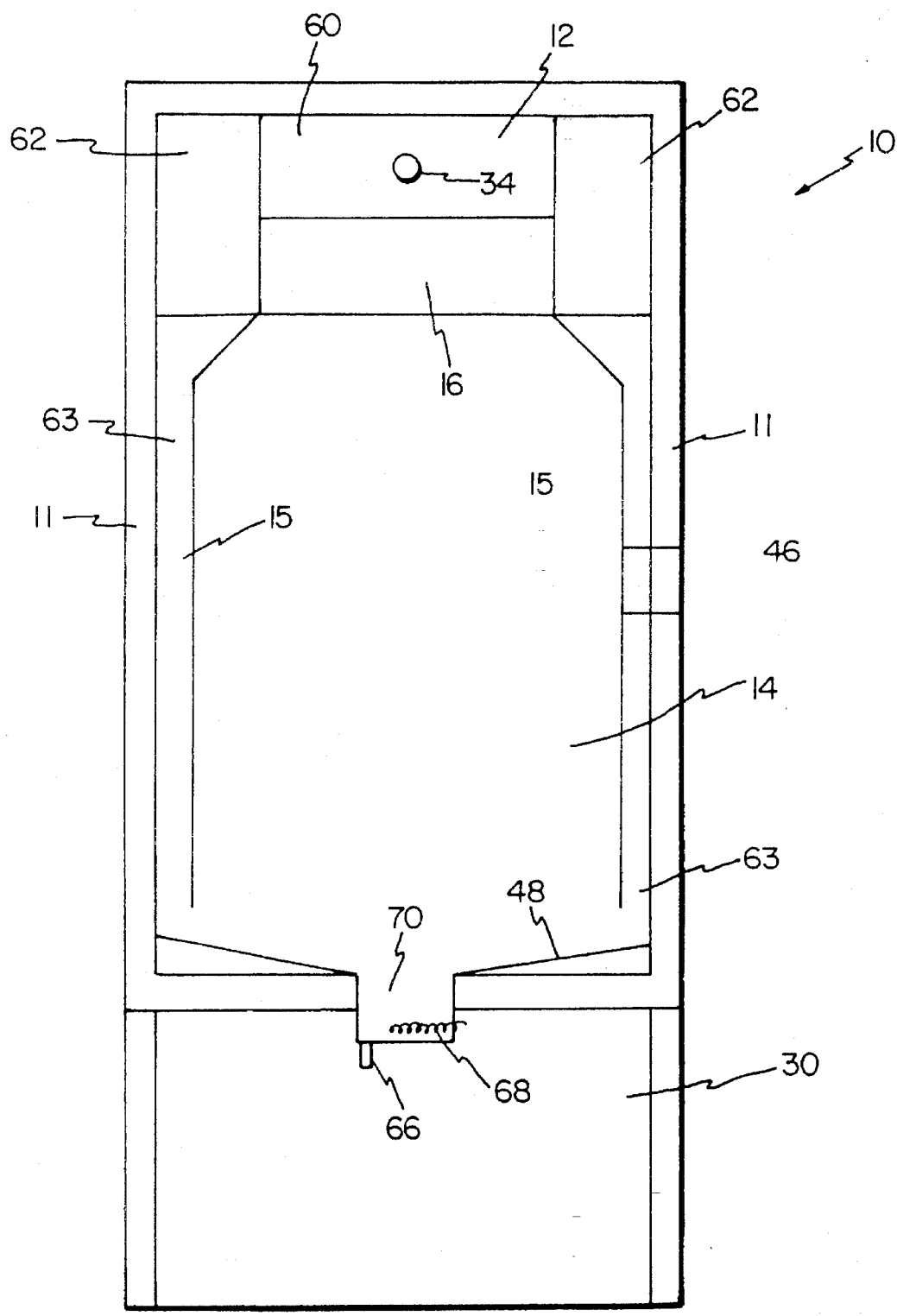
FIG. 2 is a cross sectional end view of the barrier isolation system of FIG. 1.

The floor 48 of the inner cavity 14 may advantageously be slightly sloped downwardly away from the side walls 15 and towards the entrance of the return conduit 30 as shown in FIG. 2. The cool air that is circulated through the system to cool it down after decontamination frequently causes any water vapor present to condense upon the floor 48 of the inner cavity 14. The slope of the floor 48 acts as an aid in removing this condensate by directing the condensate toward the middle of the floor for removal. A drain 66 can desirably be situated near the entrance of the return conduit 30 for draining any condensate out of the inner cavity 14 and an elongate recess 70 may extend along the middle of the floor to direct this condensate to the drain.

As an option to draining away the condensate, the recess 70 located at the entrance of the return conduit 30 may also be provided with a heating element 68, which is situated within the recess 70. During the cooling cycle, the heating element 68 can be used to boil off the condensation captured in the recess 70 and the cool air can carry the moisture out of the system.

In one particular preferred embodiment of the present invention, the barrier system 10 is adapted for use in a pharmaceutical packaging operation. In this operation, containers are depyrogenated in a depyrogenation oven such as that set forth in Melgaard's U.S. Pat. No. 4,988,288. The upper chamber 12 and return conduit 30 of the present invention are operatively connected to the hot and cool recirculating air supplies of that depyrogenation oven. This permits the precise temperature of air passing into the barrier system 10 to be controlled without requiring an entirely separate hot air supply or filtering system for the barrier system.

In use, the barrier system desirably has two modes of operation. In the first operational mode, the barrier system functions as part of a material handling system wherein equipment within the inner cavity 14 actively handles or processes a biologically-sensitive material. For example, in a typical pharmaceutical packaging system, containers are first sterilized by a known method, such as depyrogenation, before reaching the barrier system 10. Once the sterilized containers are ready for filling, they are delivered to the barrier system 10 for processing. In the processing mode, the access door 26, 28 at each end of the inner cavity 14 may be opened and the containers may be introduced to the barrier system through the first access doors 26. The containers are then transported along the cavity 14 by the conveyor means 24 to each station of the equipment for processing (such as filling and capping, as noted above). After processing, the containers are transported out of the barrier system 10 through the second access doors 28. While in this mode, cool air is desirably passed through the system to maintain a positive pressure within the inner cavity 14 and prevent any contaminants outside the barrier system from entering the system.

The second mode of operation, referred to as the decontamination mode, can be initiated in response to a number of occurrences, including the completion of a pre-set number of handling operations or the detection of an unacceptable level of contaminants within the system.

Before the initiation of the cleansing process, the normal operation mode is first terminated and all temperature sensitive materials are removed from the housing. The access doors 26 are then sealed and hot air, which may be provided by an associated depyrogenation oven as noted above, is introduced into the upper chamber 12 through the damper 44. The hot air source preferably provides heated air at a temperature of greater than about 100° C. with a temperature of about 120° C. being preferred. The heated air stream passes from the upper chamber 12, through the filters 16, and into the cavity 14, thereby gradually heating up the filters. The air stream then travels around the material handling equipment and into the return conduit 30 where it is directed up the channel 32 and out of the barrier system 10 to be returned to the heating source.

The air recirculation loop continues until the system's internal equipment, and particularly the filters 16, are heated to a sufficient temperature (e.g. at least about 100° C.) so that steam will not condense on the equipment or, perhaps more importantly, in the filters during the decontamination process. The air stream desirably passes through the filters 16 in a laminar flow pattern, as noted above, so that the filters 16 are uniformly heated.

Once the internal parts of the isolation system have reached at least about 70° C., saturated steam may be passed through the steam conduit 34 and into the upper chamber 12. A steam flow rate of about 2 lbs/ft$^2$ of steam per hour has yielded acceptable results. When the saturated steam is introduced into the inner cavity 14, it is desirable to maintain the environment within the barrier system at a greater positive pressure than adjacent environments to prevent any contaminants that may be outside the barrier system from entering the system during the decontamination process.

As noted above, it may be advantageous to introduce hydrogen peroxide to the steam supply. The concentration of hydrogen peroxide in the steam supply may be varied within a rather broad range. However, it has been found that injecting hydrogen peroxide into the steam supply at a rate of between about 40 and 70 milligrams of peroxide per minute per liter of chamber volume is optimal. Although greater concentrations of hydrogen peroxide could be used, this could adversely affect some particularly sensitive products. As explained more fully below, the 40–70 milligram injection rate has proven to substantially reduce the time necessary to decontaminate the equipment within the inner chamber 14 and no significant adverse effects upon the quality of most products would be expected at this concentration.

The internal parts of the barrier system 10 are exposed to the saturated steam or steam and hydrogen peroxide for a period sufficient to decontaminate them to the desired degree. If a high degree of decontamination is required, i.e. if the probability of contamination must be very low, the time of exposure to the saturated steam environment should be longer; if the possibility of contamination is less of a concern, this time may be shorter. Afterwards, the internal parts are cooled by passing cool air through the system, such as by passing the air past a cooling coil and into the recirculation loop 38.

The barrier system 10 is also desirably equipped with glove ports 46 so that minor adjustments and other needed operational actions can be accomplished without exposing the inner cavity 14 to contamination. The ports 46 are desirably positioned in the side walls 15 of the housing at a location which allows for access to the equipment within the inner cavity 14. In the preferred embodiment, the ports 46 are sealed from the outside environment to prevent contaminate from entering the sterilized system.

Figure 3:
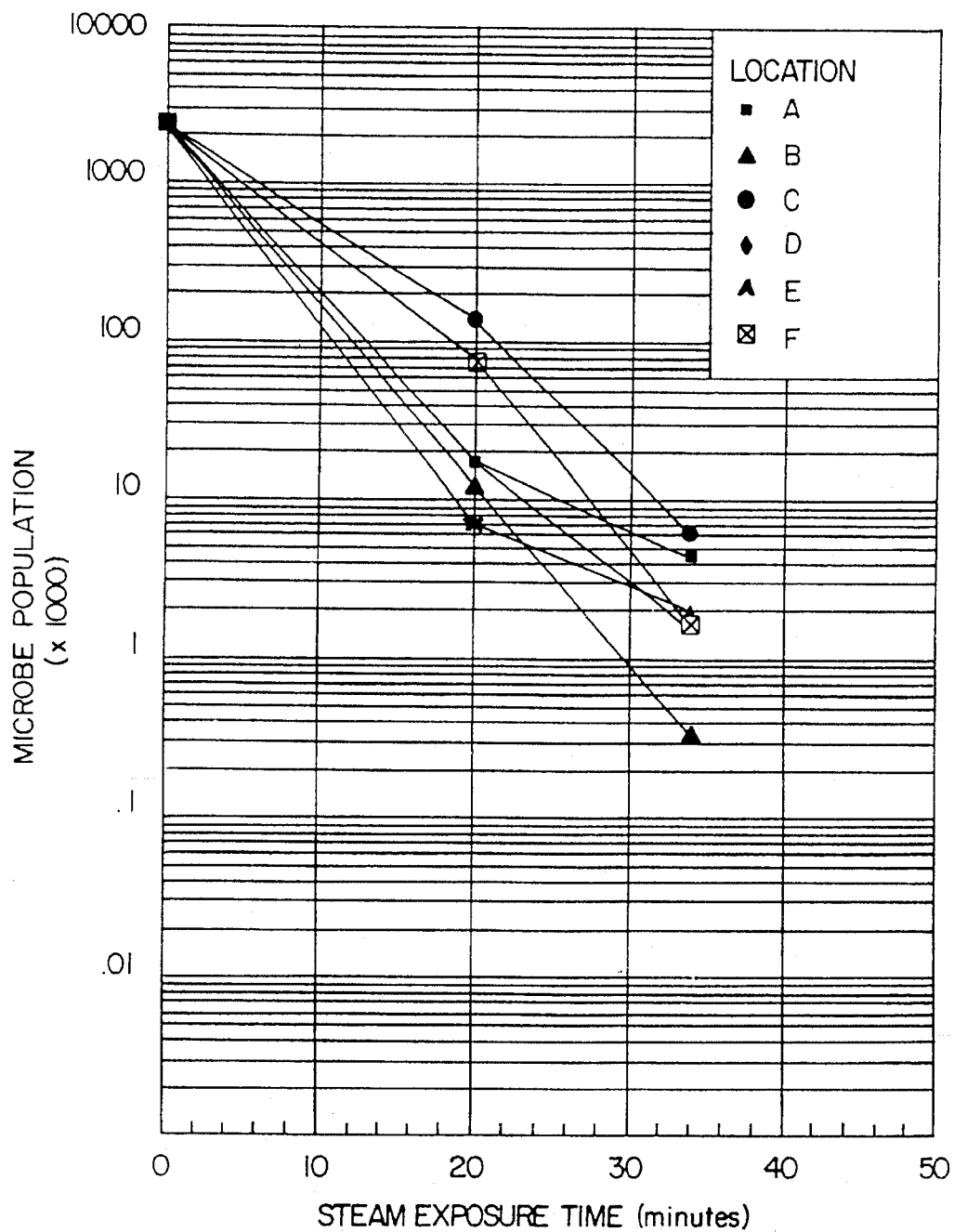
FIG. 3 is a graph showing a relationship between the surviving microbe population as a function of the steam exposure time.

In order to test the efficacy of the invention, a barrier isolation system substantially as depicted in FIGS. 1 and 2 was constructed and tested; the graph of FIG. 3 shows the results of those tests. For the tests, the barrier isolation system was constructed and equipment for filling containers with liquid pharmaceuticals was placed within the system. A known population of a common microbe, Bacillus Macerans, was placed at each of some six different sites within the inner cavity (denoted as lines A-F). As shown in FIG. 3, the initial level of this artificially introduced microbe was measured as about $3 \times 10^{10}$.

The access doors were sealed and hot air of approximately 120° C. was introduced into the upper chamber and passed through the system. After the filters were heated to approximately 120° C., saturated steam was introduced into the upper chamber and through the system through use of the air recirculation loop. As shown in FIG. 3, the time in which the interior of the system was exposed to the steam environment was varied and the population of viable microbes was measured at each of the six different locations A-F.

The data in FIG. 3 indicates that a generally logarithmic relationship exists between the length of time that the equipment was exposed to the saturated steam environment and the resultant reduction in the level of the *Bacillus Macerans* microbe. The results of this graph also indicate that the population of the microbe was reduced by a factor of about 1000 ($10^3$) at essentially all of the locations of the interior cavity after about 35 minutes in the saturated steam environment.

A similar test was run using a combination of hydrogen peroxide and steam as the decontaminating agent. In this test, a known population of the microbe *Bacillus Sterothermophilus* was used in place of the *Bacillus Macerans* used in the previous test. Bacillus Sterothermophilus is generally acknowledged as being a somewhat tougher microbe to eliminate then the *Bacillus Macerans*.

A known population of the *Bacillus Sterothermophilus* was introduced at a single location within the inner cavity 14. Once again, the access doors were sealed and the system was preheated to approximately 120° C. A 35% solution of hydrogen peroxide in water and pressurized steam were passed through an atomizer and mixed with the saturated steam supply prior to introducing the combined hydrogen peroxide/steam into the steam delivery tube 34, substantially as described above The hydrogen peroxide solution was introduced to the atomizer at a rate of about 100–200 ml/min.

The population of the microbe was rather rapidly reduced. In this test, an initial population of more than 10 million was reduced to less than 100 in less than 15 minutes. The data in FIG. 3 show that saturated steam used in connection with the present invention can reduce the population of *Bacillus Macerans* by a factor of about $10^3$ within about 35 minutes. Clearly, the reduction by a factor of better than $10^5$ in less than 15 minutes achieved by utilizing hydrogen peroxide with the steam can significantly reduce the time required to effectively decontaminate the system.

In order to further demonstrate the effectiveness of the combined hydrogen peroxide/steam decontamination agent used with the present barrier system, a second test was run using superheated steam at 250° F. as a decontaminating agent. an initial population of approximately 4 million was reduced to approximately 40 over the course of slightly less than 30 minutes. Although this also represents a reduction in the population of the Bacillus Sterothermophilus microbe by factor of about $10^5$, the use of even superheated steam (as opposed to the saturated steam at 212° F. used above in connection with FIG. 3) took more than twice as long to achieve approximately the same degree of decontamination.

Although it will take some time to preheat the system before introducing the steam and to cool it back down for standard operation, the present invention greatly reduces the total down time of the system associated with decontamination operations. If the product being packaged is particularly sensitive to chemicals such as hydrogen peroxide, the present invention can be operated with saturated steam alone. Utilizing hydrogen peroxide with the steam can further reduce the down time, though:

While a preferred embodiment of the present invention has been described, it should be understood that the various changes, adaptations and modifications may be made therein without the parting from the spirit of the invention and the scope of the appended claims.

What is claimed is:

1. A barrier isolation system for decontaminating parenteral drug equipment, comprising:

a decontamination housing;

at least one filter extending generally horizontally along a length of the interior of said housing, said at least one filter dividing said housing into an upper chamber and a lower cavity, said lower cavity for containing equipment to be decontaminated;

a steam conduit in fluid communication with said upper chamber for providing steam to said upper chamber, said steam passing through said at least one filter to reach said inner cavity;

heated gas circulation means for introducing heated gas at a temperature of at least 100° C. into said upper chamber and for circulating the heated gas through said at least one filter to heat said at least one filter to prevent condensation thereon, said circulation means including a return conduit in communication with said lower cavity.

2. The invention of claim 1 further comprising a means for introducing hydrogen peroxide into the steam.

3. The invention of claim 2 wherein the means for introducing hydrogen peroxide comprises an atomizer for atomizing the hydrogen peroxide within the steam.

4. The invention of claim 2 wherein the means for introducing hydrogen peroxide includes means for selectively controlling the flow of hydrogen peroxide into the steam.

5. The barrier isolation system of claim 1 wherein the lower cavity includes an exit and an entrance and access doors for allowing the entrance and exit of containers into the lower cavity.

6. The barrier isolation system of claim 5 wherein the access doors contain transparent windows for viewing the lower cavity.

7. The barrier isolation system of claim 6 wherein the system includes glove ports for accessing the equipment without exposing the system to the outside environment.

8. The barrier isolation system of claim 1 wherein the lower cavity includes an exit and an entrance and access doors for allowing the entrance and exit of containers into the lower cavity.

9. The barrier isolation system of claim 8 wherein the access doors contain transparent windows for viewing the lower cavity.

10. The barrier isolation system of claim 9 wherein the system includes glove ports for accessing the equipment without exposing the system to the outside environment.

11. A method for decontaminating equipment comprising the steps of:

a) providing a decontamination housing and a filtering means extending generally horizontally along a length of the interior of said housing, said filtering means dividing said housing into an upper chamber and a lower cavity;

b) introducing gas heated to a temperature above 100° C. into said upper chamber and circulating said heated gas through said filtering means into the lower cavity until the filtering means and equipment contained in said lower cavity reach a temperature of no less than 70° C.;

c) introducing a decontaminating gas into said upper chamber and passing the decontaminating gas through the filtering means into said lower cavity for a time effective to decontaminate said equipment in said lower cavity.

12. The method of claim 11 further comprising the step of introducing hydrogen peroxide into said decontaminating gas.

13. The decontaminating method of claim 11 further comprising the step of boiling off condensation in said lower cavity to remove excess condensation through the use of a heating element located underneath the lower cavity.

14. The decontaminating method of claim 11 wherein the heated gas is air, and further comprising the step of:

d) circulating cooling air through the filtering means and lower cavity to cool the filtering means and equipment.

15. The decontaminating method of claim 11 further comprising the step of circulating the heated and cool air out of the lower cavity through air ducts located adjacent to the upper chamber.

16. The decontaminating method of claim 15 further comprising the step of draining condensation out of the lower portion of the lower cavity.

* * * * *